United States Patent [19]

Mikhail et al.

[11] Patent Number: 5,097,847
[45] Date of Patent: Mar. 24, 1992

[54] EXTREMITY SHEET AND LEG HOLDER COMBINATION

[76] Inventors: W. E. Michael Mikhail, 4203 Shamley Green, Toledo, Ohio 43623; Henrietta K. Morris, 3603 Big BearLake, Arlington, Tex. 76016

[21] Appl. No.: 655,763

[22] Filed: Feb. 14, 1991

Related U.S. Application Data

[63] Continuation-in-part of Ser. No. 495,649, Mar. 19, 1990, abandoned.

[51] Int. Cl.⁵ .................. A61B 19/00; A61B 19/08
[52] U.S. Cl. ................................. 128/849; 128/853
[58] Field of Search .......................... 128/849-856

[56] References Cited

U.S. PATENT DOCUMENTS

| | | | |
|---|---|---|---|
| 1,554,692 | 9/1925 | Shane | 128/849 |
| 3,717,144 | 2/1973 | Bimler | 128/88 |
| 3,741,206 | 6/1973 | Binard | 128/853 |
| 3,881,474 | 5/1975 | Krzewinski | 128/852 |
| 4,040,418 | 8/1977 | Collins | 128/852 |
| 4,327,714 | 5/1982 | Spann | 128/891 |
| 4,388,920 | 6/1983 | Hajost et al. | 128/80 C |
| 4,476,860 | 10/1984 | Collins | 128/853 |
| 4,553,538 | 11/1985 | Rafelson | 128/852 |
| 4,730,609 | 3/1988 | McConnell | 128/853 |
| 4,745,915 | 5/1988 | Enright | 128/853 |
| 4,890,628 | 1/1990 | Jackson | 128/853 |
| 4,905,710 | 3/1990 | Jones | 128/849 |
| 4,957,120 | 9/1990 | Grier-Idris | 128/849 |

Primary Examiner—Robert A. Hafer
Assistant Examiner—Michael Brown
Attorney, Agent, or Firm—Emch, Schaffer, Schaub & Porcello Co.

[57] ABSTRACT

A combination extremity sheet and leg holder is provided for supporting the leg of a patient in various positions during various phases of knee surgery.

46 Claims, 7 Drawing Sheets

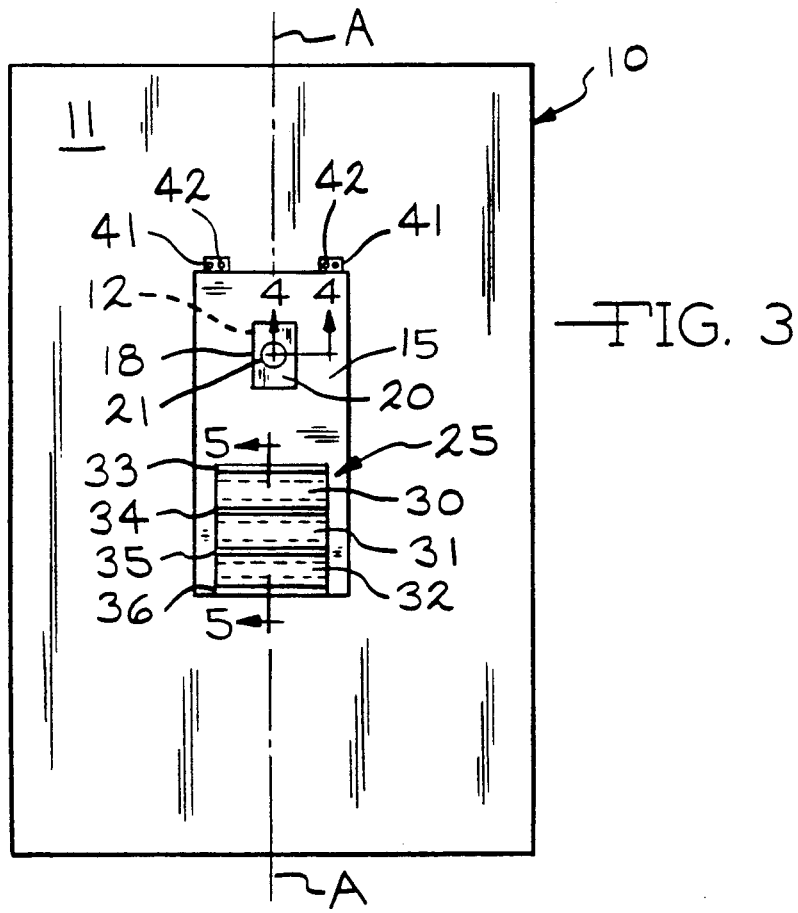
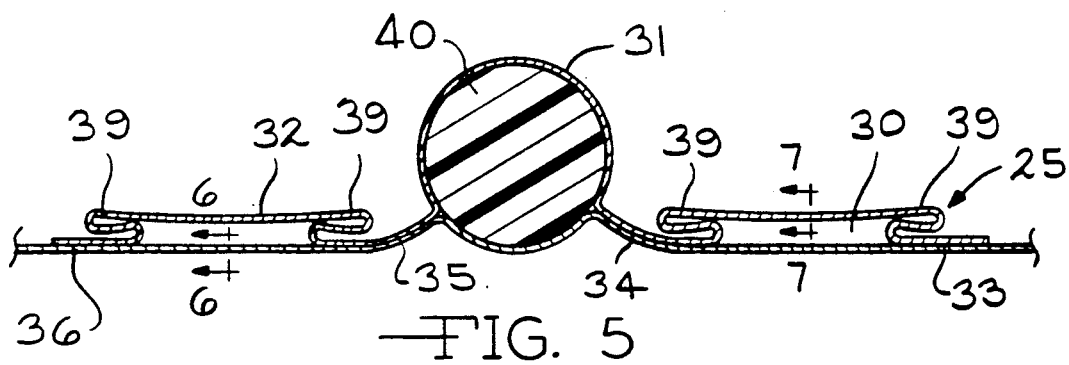
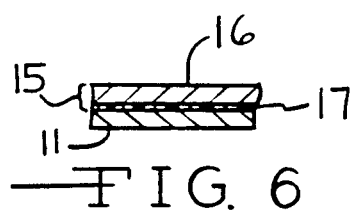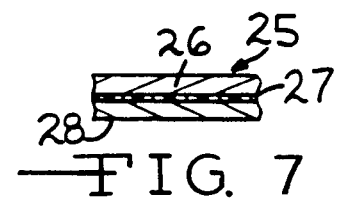
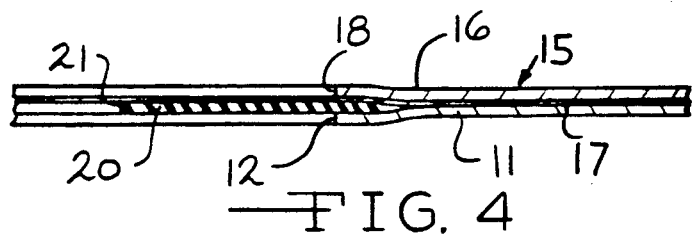

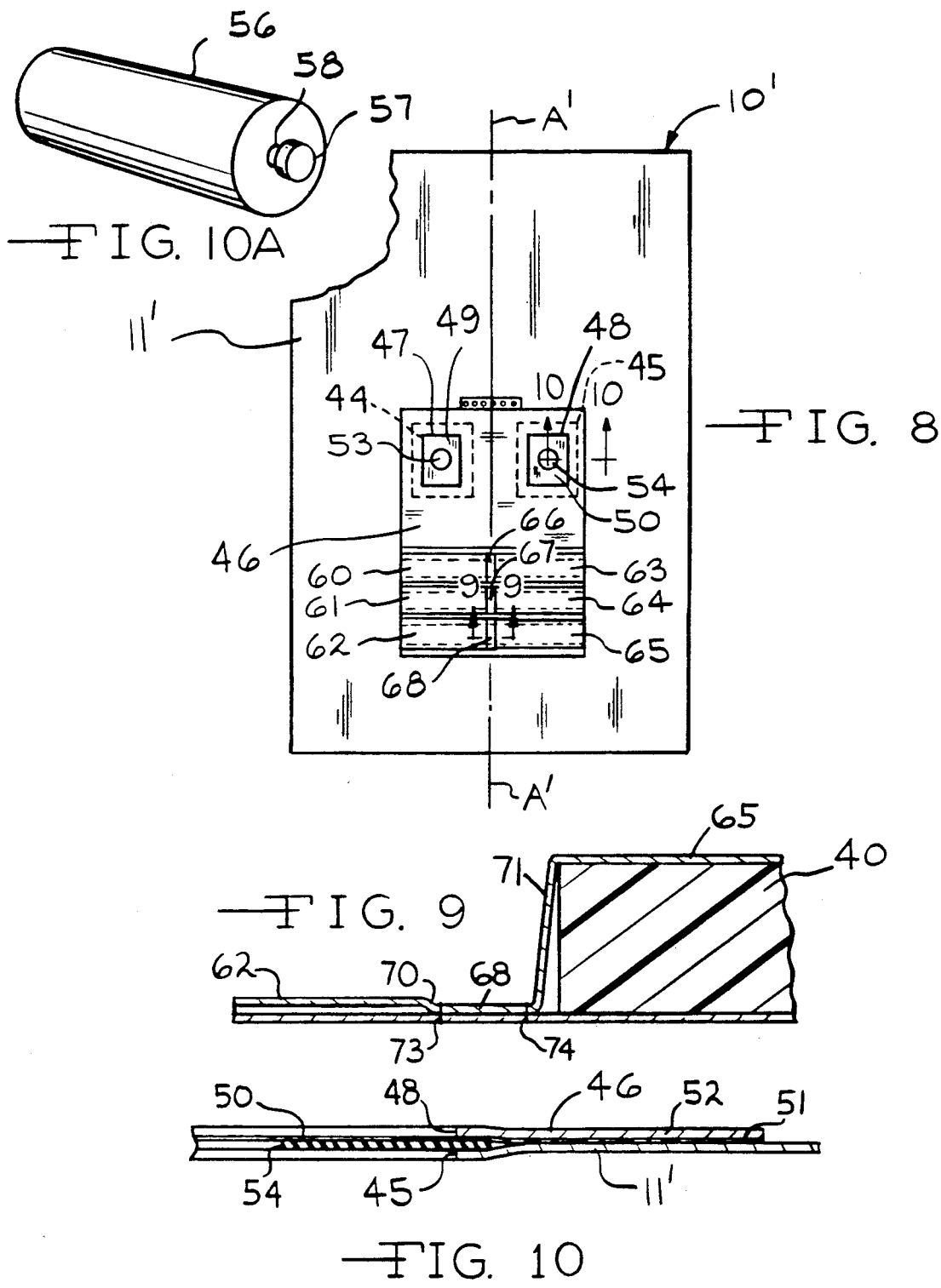

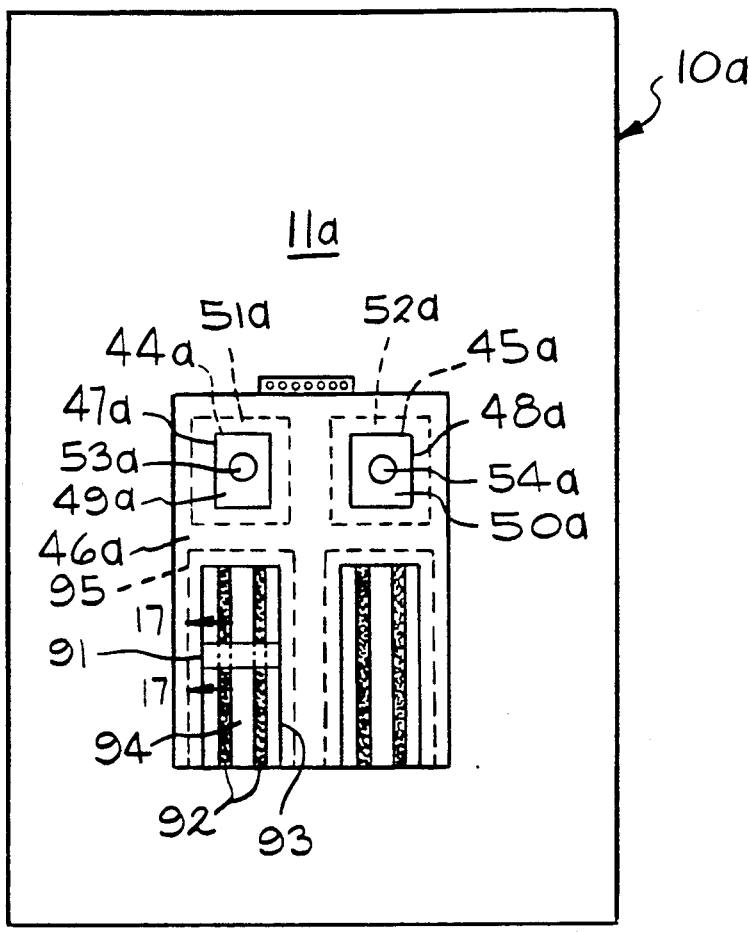
FIG. 16
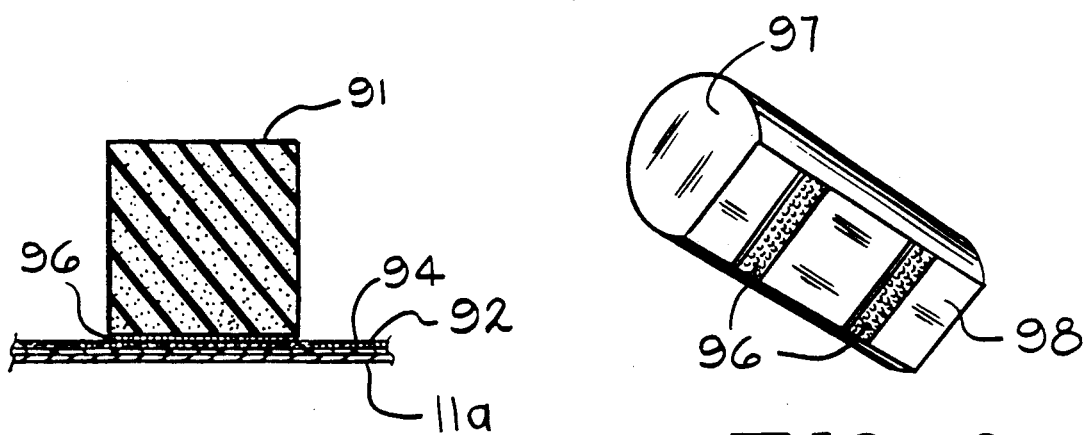
FIG. 17
FIG. 18

1

EXTREMITY SHEET AND LEG HOLDER COMBINATION

CROSS REFERENCE TO RELATED APPLICATION

This application is a continuation-in-part to application Ser. No. 07/495,649 filed Mar. 19, 1990, now abandoned.

BACKGROUND OF THE INVENTION

In performing knee surgery, it is desirable to position the leg of the patient in one or more desired locations so that the knee upon which surgery is being performed is disposed at a specific desired angle during the surgery or at varying positions during various phases of the surgery. A number of prior art patents disclose various types of supports to accommodate varying positions of a patient's knee. For example, U.S. Pat. No. 4,388,920 (incorporated herein by reference) discloses a Variable Position Knee Immobilizer which includes a flexible cover having upper and lower planar sections adapted to be wrapped around a patient's leg and having (1) means for securing the cover around the patient's leg above and below the knee and (2) stiffener support sections above and below the knee pivotally connected at the middle of the knee to vary the angle between the sections. Means are provided to lock the stiffener support sections in varying positions. U.S. Pat. No. 3,717,144 discloses an Orthopedic Leg Supporting Appliance comprising several supports for upper and lower parts of a leg of a patient arranged to be capable of being articulated in relation to each other.

SUMMARY OF THE INVENTION

The present invention relates to a combination extremity sheet and leg holder for use in performing orthopaedic surgery. More specifically it is designed for use in positioning the leg of a patient during knee surgery. The combination extremity sheet and leg holder may have a generally rectangular shape and comprises a first cover sheet of flexible material having a rectangular or other shaped cutout, a panel portion consisting of a second sheet of material of larger size than said cutout adhered or otherwise fastened to the cover sheet and overlying said cutout, said second material having its own cutout aligned with the cutout of the cover sheet material and a third sheet formed of rubber or other stretchable material adhered to and positioned in the aligned cutouts of the cover sheet and second panel sheet, said stretchable third sheet having an aperture for receiving the leg of a patient. The combination extremity sheet and leg holder further includes one or more pockets for receiving a cylindrical or other shaped pillow or foot support located in alignment with the leg of a patient extending through said aperture. The foot support may be positioned in one of the pockets to support the patient's heel with the patient's knee bent in one or more desired positions for surgery. If desired, straps or other types of engagement means may be provided for fastening the pillow or foot support to the cover sheet or panel in lieu of the pockets and the first cover sheet and possibly even the panel portion may have a split or rectangular notch to receive the patient's leg in lieu of the cutouts and the stretchable third sheet with its aperture. All components should be sterilizable. The combination including the pillow may be disposable; however, it could be reusable if formed from washable, sterilizable components.

BRIEF DESCRIPTION OF THE DRAWINGS

Referring now to the drawings:

FIG. 3 is a top plan view of the combination extremity sheet and leg holder of the present invention.

FIG. 4 is a sectional view taken through line 4—4 of FIG. 3.

FIG. 5 is a sectional view taken through line 5—5 of FIG. 3 and showing the pillow or foot support member thereof positioned in one of the of pockets.

FIG. 6 is a sectional view taken through line 6—6 of FIG. 5.

FIG. 7 is a sectional view taken through line 7—7 of FIG. 5.

FIG. 8 is a plan view of a modified embodiment of my invention.

FIG. 9 is a sectional view taken through line 9—9 of FIG. 8 showing a pillow placed in one of the pockets.

FIG. 10 is a sectional view taken through line 10—10 of FIG. 8.

FIG. 10A is a perspective view showing a pillow with a contoured gripping feature.

FIG. 16 is a top plan view of a further modified embodiment of the combination extremity sheet and leg holder.

FIG. 17 is a sectional view taken through line 17—17 of FIG. 16.

FIG. 18 is a perspective view of the pillow portion of the embodiment shown in FIG. 16 but having a different shape.

DESCRIPTION OF THE PREFERRED EMBODIMENTS

Figure 1:
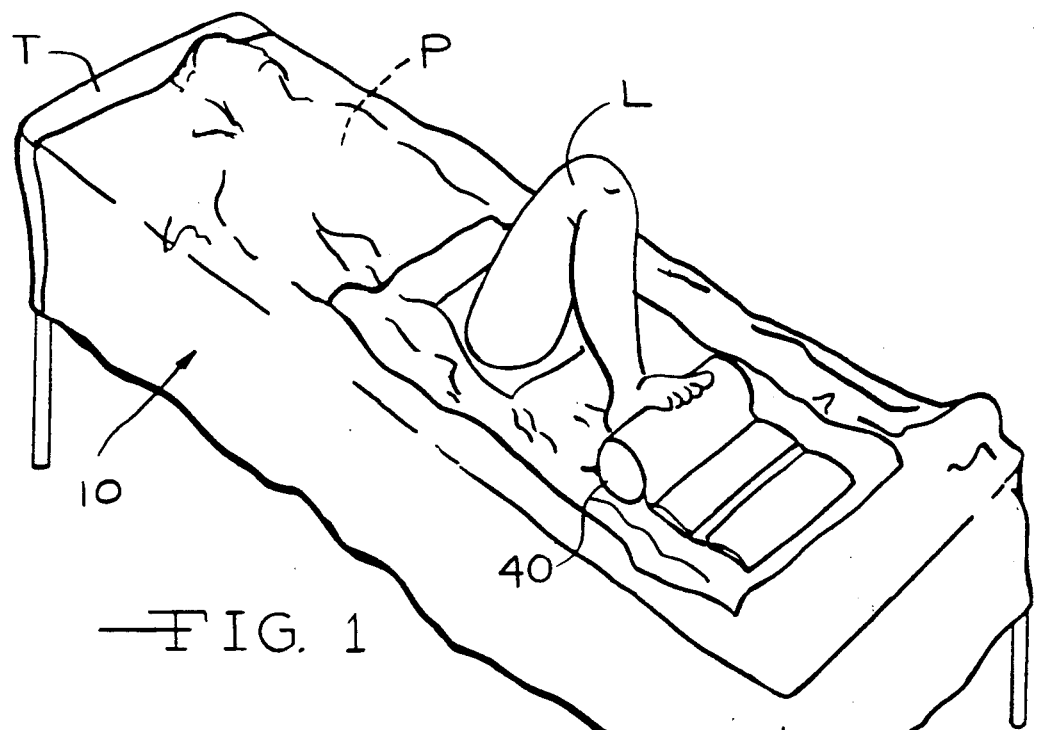
FIGS. 1 and 2 are perspective views showing the combination extremity sheet and leg holder of the present invention in use on a patient and showing the patient's leg in different positions.
Figure 2:
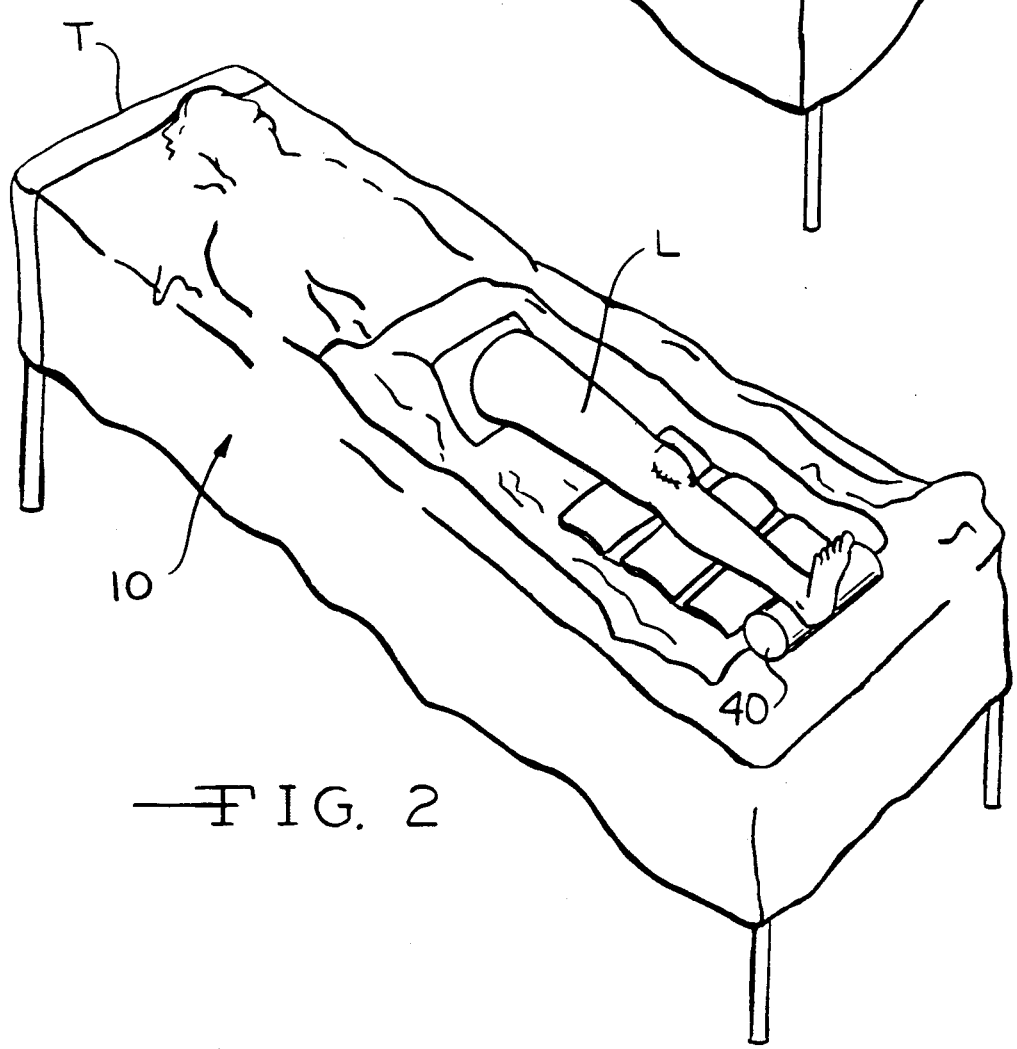

Referring now to FIGS. 1 and 2, there is shown a combination extremity sheet and leg holder generally designated by the numeral 10 positioned on a patient P whose leg L extends through an opening in the sheet 10. The patient P is supported on an operating table T.

The combination extremity sheet and leg holder 10 includes a first or cover sheet 11 formed of any desired flexible, sterilizable non-woven or woven fabric material such as linen or other cloth, plastic or combination material. The cover sheet 11 may have any one of a wide variety of sizes and configurations; however, it is usually rectangular and large enough to entirely cover the patient. The cover sheet 11 has a rectangular cutout 12 formed generally in an area to be aligned with the upper portion of the patient's leg L. A second sheet or panel member 15, preferably having a rectangular configuration, and of a smaller size than the cover sheet 11, is sewn or adhesively or otherwise secured to the cover sheet 11. The panel member 15 has a rectangular cutout 18 which is aligned with the cutout 12 of the cover sheet 11 and is, preferably, the same size as the cutout 12. (See FIGS. 3 and 4).

In the embodiment shown in FIGS. 3-7, the panel member 15 is multi-ply and includes a first or upper ply 16 of a linen or other type fabric and a lower film ply 17 formed of blown plastic film such as low density polyethylene film. The panel member 15 must, of course, be sterilizable. If desired, the panel member 15 could be formed or a single ply rather than multiple plies; however, it should be formed of material which is strong enough to withstand, without tearing, the stresses imparted to it when the patient's leg L is disposed in any of the desired positions.

As can be seen in FIG. 4, the film ply 17 is fastened directly to the cover sheet 11. Although FIGS. 4-7 shows the film ply 17 and, hence, the panel member 15 as being adhesively adhered to the cover sheet 11, it should be understood that the panel member 15 may be sewn or otherwise connected to the cover member 11. The rectangular cutout 18 of the panel member 15 extends through both the upper ply 16 and the film ply 17.

Positioned within but extending beyond the opening defined by the aligned rectangular cutouts 12 and 18 of the cover sheet 11 and panel member 15, respectively, is a third sheet member 20 formed of a thin sheet of rubber or other resiliently stretchable material. The third sheet member 20 preferably is produced from a block polymer marketed under the name Kraton ®, a registered trademark of Shell Oil Company. As shown in FIG. 4, the third sheet member 20 is sandwiched between the cover member 11 and panel member 15. It may be retained therebetween by any suitable adhesive means. If desired, the third sheet member 20 could be sewn or heat sealed between such cover member 11 and panel member 15.

The third sheet member 20 has a circular aperture 21 approximately three inches in diameter through which a patient may insert his or her foot and leg. Since the third sheet member 20 is formed of readily stretchable, resilient material, it will be able to be stretched over a leg of a patient up to the upper portion of the thigh and can be snugly engaged thereto. Obviously, the aperture 21 could be larger for persons of very large size or smaller to accommodate the smaller legs of children. As can be seen in FIG. 3, the aperture 21 lies on the centerline or longitudinal axis A of the panel member 15.

As may be seen from the drawings, there is provided means for supporting the foot of the patient P in a number of different positions ranging from substantially fully bent as shown in FIG. 1 to straight as shown in FIG. 2. Such means for supporting the foot in one of a number of positions includes a flexible looped member 25 adhered to the panel member 15. The looped member 25 may be formed of the same type material as the panel member 15. Alternatively, as shown in FIG. 7, it may be formed of three plys consisting of an outer ply 26 formed of fabric, a center ply 27 formed of plastic film and an inner ply 28 formed of fabric.

The looped member 25 has selective portions sewn, adhered or otherwise fastened to the panel member 15 such that a series of pockets 30, 31 and 32 are formed. As can be seen particularly in FIGS. 3 and 5, the pockets 30, 31 and 32 are aligned centrally on the axis A, extend at right angles to such axis A and are spaced at varying distances from the aperture 21. The portions of the looped member 25 which are fastened to the upper ply 16 of the panel member 15 define a series of rows 33, 34, 35 and 36 which also extend perpendicular to the longitudinal axis A. The rows 33, 34, 35 and 36 are separated by and define the opposite sides of the pockets, with the pocket 30 being between the rows 33 and 34, the pocket 31 being between the rows 34 and 35 and the pocket 32 being between the rows 35 and 36.

In preparing the looped member 25 for fastening to the panel member 15, excess material is gathered to form an accordion pleat 39 of the excess material beyond that needed to simply span the distance between the respective sets of rows 33-34, 34-35 and 35-36. Thus, the distance between the rows 33 and 34 is approximately 5 inches and yet the length of the looped member 25 utilized, in cooperation with the panel member 15, to form the pocket 30 is approximately ten inches. Such construction permits the respective pockets 30, 31 and 32 to be opened in order that they may receive a cylindrical or other shaped pillow 40. As shown in FIG. 5, the pillow 40 is placed in the second or center pocket of 31 while in FIG. 1, the pillow 40 is positioned in the first pocket 30 closest to the patient's hip.

The width of the looped member 25 is approximately 16 inches. Thus, each of the pockets is approximately 16 inches long. As shown in the drawings, the pockets 30, 31 and 32 are open on both ends. If desired, one end of the pockets may be sewn shut or otherwise closed.

The pillow 40 is a sterilizable tube of suitable material such as foam plastic or other suitable material which may be readily cleaned and sterilized.

Since the extremity sheet and leg holder combination are used in an operating room, both the sheet 10 and the pillow 40 will usually be disposed of after a single use. However, it is within the scope of this invention that either or both of the sheet 10 or the pillow 40 could be reused. In order for any such component to be reused, it must be washable and sterilizable.

The pillow 40 is approximately 4 inches in diameter and 11 inches long. For an extremity sheet and leg holder combination for a person of average size, say 5 to 6 feet in height, the distance from the center of the aperture 21 of the third sheet member 20 to the center of the first pocket 30 closest to the patient's hip is approximately 19 inches. Alternatively, the pillow 40 could be inflatable. Additionally, as shown in the embodiment of FIG. 10A, there could be provided a pillow 56 having an integrally formed knob 57 extending from one end and having a reduced size from the main portion of the pillow 56 and spaced therefrom by a smaller stem 58 for convenience of gripping. In lieu of the knob 57, other types of gripping means may be provided for the pillow 56 such as finger receiving holes or depressions.

If desired, the panel member 15 may be provided with a pair of tabs 41 having holes 42. Additionally, if desired, the panel member 15 could be much shorter, extending only a short distance beyond the extremities of the cutout 12 of the cover sheet 11. In that case, the looped member 25 would be fastened directly to the cover sheet 11. In that event, the cover sheet would have to be formed of a material strong enough to withstand the stresses imparted to it when the patient's leg is disposed in any of the desired positions.

Referring now to FIGS. 8, 9 and 10 there is shown a modified combination extremity sheet and leg holder 10' which can be used for a patient having surgery on both knees at the same time. In that embodiment, there is provided a first cover sheet 11' substantially identical to the first cover sheet 11 of the previous embodiment and a panel member 46 made of material substantially identical to that of the panel member 15. In the embodiment of FIGS. 8, 9 and 10, the cover sheet 11' is provided with a pair of cutouts 44 and 45 which are located on opposite sides of the axis A' by approximately the same distance. As can be seen from FIG. 8, the respective cutouts 44 and 45 are aligned with one another in the direction normal to the axis A'. If desired, a single large cutout spanning the distance needed to accommodate both knees of a patient may be provided instead of the two cutouts 44 and 45 as shown in FIG. 8.

In this embodiment there is also provided a panel member 46 having a pair of cutouts 47 and 48, each of which is aligned with the respective cutouts 44 and 45 of the cover sheet 11'.

Positioned within each of the cutouts 47 and 48 are a pair of identical third sheet members 49 and 50 formed of the same type of stretchable, resilient rubber film as third sheet member 20 of the embodiment of FIGS. 1-7. As can be seen from FIG. 10, the third sheet member 50 is sandwiched between and adhered to the cover sheet 11' and the panel member 46. The panel member 46 may be multi-ply and include a thin sheet of film plastic 51 adhered to a sheet 52 of cloth. As shown, it is sheet plastic film portion 51 of the panel member 46 which is in direct contact with the third sheet member 50 and with the cover sheet 11'.

Each of the third sheet members 49 and 50 is provided with an aperture, 53 and 54 respectively, to receive a leg of the patient. Although the spacing between the apertures 53 and 54 could vary if the combination extremity sheet and leg holder 10' were intended for a young child or a very large person, center to center spacing of approximately 21 inches will be satisfactory for most patients.

As will be appreciated if the cover sheet 11' is provided with a single enlarged cutout rather than the two cutouts 44 and 45 as shown, it will be necessary that the third sheet member also be enlarged so that its entire peripheral edge may be sandwiched between and adhered to both the sheet 11' and the panel member 46.

As can be seen from FIG. 8, there are also provided a plurality of pockets 60, 61 and 62 aligned with the aperture 53 and pockets 63, 64 and 65 aligned with the aperture 54. These are constructed in similar manner to the pockets 30, 31 and 32 of the first embodiment of FIGS. 1-7. Although the respective pairs of pockets 60 and 63, 61 and 64, 62 and 65 could each extend the full width of the panel member 46 to form three pockets each having a length approximately double the length of the respective pockets 60, 61 and 62, preferably, they are separated as by sewing, adhering or otherwise fastening a center strip as at 66, 67 and 68 in between each of the respective sets of pockets 60 and 63, 61 and 64, 62 and 65. Thus, as shown in FIG. 9, each of the pockets 62 and 65 will then have closed ends 70 and 71 adjacent the longitudinal axis A'. As shown in FIG. 9 the center strip 68 is defined by sewn stitching 73 and 74.

Figures 11, 15:
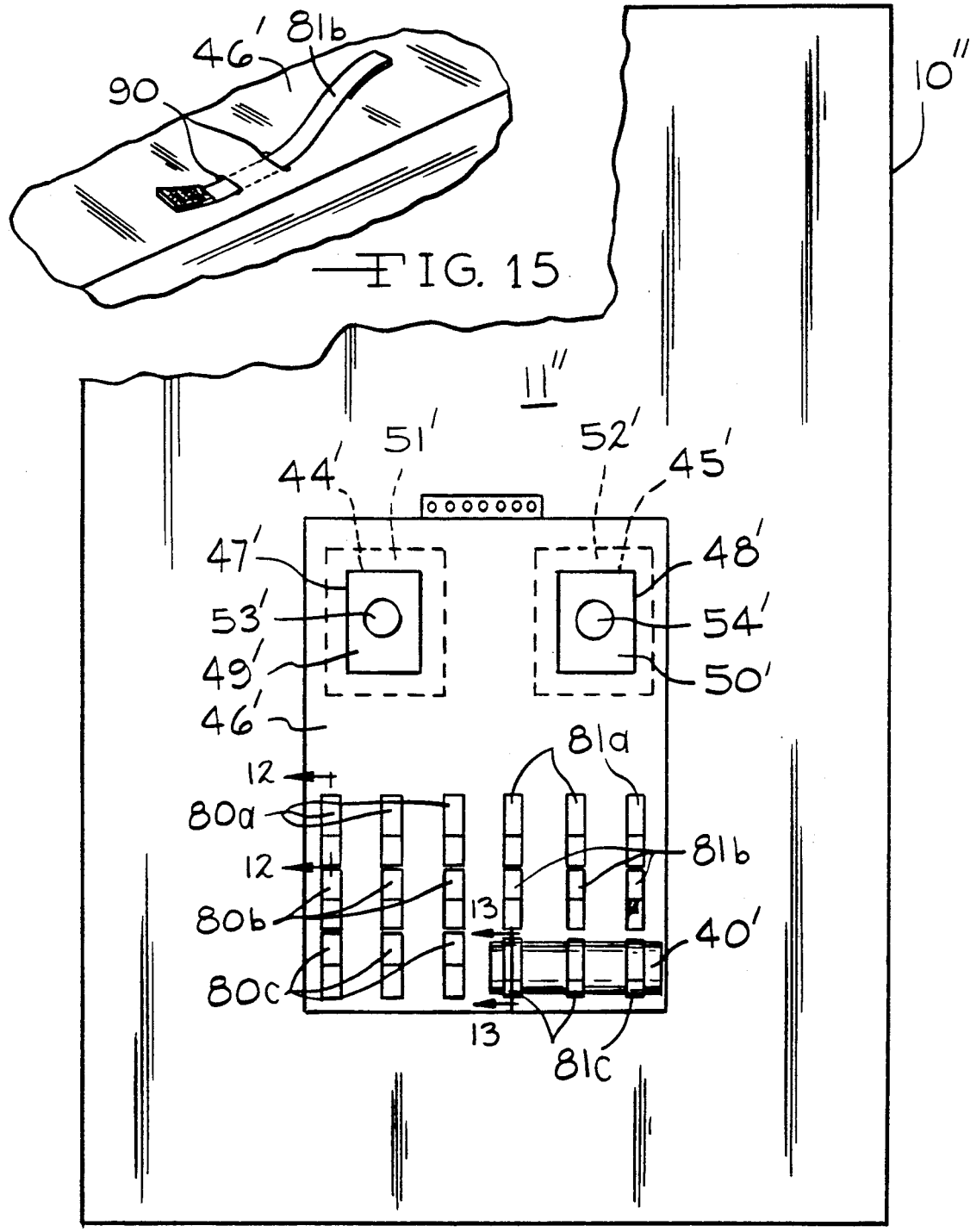
FIG. 11 is a top plan view of a modified embodiment of the combination extremity sheet and leg holder.
FIG. 15 is a fragmentary perspective of another embodiment.

Referring now to FIGS. 11-14, there is shown as additional embodiment which utilizes a different means for connecting the pillow or foot support to the cover sheet. The modified combination extremity sheet and leg holder 10" includes a first cover sheet 11" similar to the cover sheet 11 of the embodiment of FIGS. 1-7 and a pillow 40' similar to the pillow 40. The cover sheet 11" has at least one rectangular cutout 44' or other means for receiving a patient's leg therethrough. As shown in FIG. 11, there are two rectangular cutouts 44' and 45' illustrating an embodiment which would be used for a patient having surgery on both knees at the same time. However, it should be understood that the embodiment of FIGS. 11-14 and the means for fastening a pillow 40' or other foot support to the sheet 11" may be used irrespective of whether it has one cutout 44' and is one intended for performing surgery on one leg of the patient or has two cutouts or other means for receiving a patient's legs and is intended for performing surgery on both legs of a patient.

A panel member 46' is secured to the cover sheet 11".

There is also provided a pair of cutouts 47' and 48' in the panel member 46'. Positioned within each of the cutouts 47' and 48' are a pair of identical third sheet members 49' and 50'. The sheet members 49' and 50' are formed of a thin sheet of rubber or other resiliently stretchable material and are each provided with an aperture 53' and 54', respectively, each of which will receive a leg of a patient. The third sheet members 49' and 50' extend outwardly beyond their respective sets of aligned cutouts 44', 47' and 45', 48' and have their respective edge portions 51', 52' adhesively connected or sewn or otherwise secured to the first cover sheet 11" or the panel member 46' or, preferably to both.

As can be seen in FIG. 11, the pillow 40' or other foot support means is aligned with the apeture 54'. As will be appreciated from the description of the previous embodiments, a second pillow (not shown) will be position in alignment with other aperture 53'.

The modified means of supporting the pillow 40' on the second sheet member 46' includes three sets of strap members 80a, 80b, and 80c, aligned with the aperture 53' at varying distances therefrom and three sets of strap members 81a, 81b and 81c, in alignment with the second aperture 54' at varying distances therefrom. Although each set of straps 80a, 80b, 80c, 81a, 81b and 81c, is shown as consisting of three separate straps; however, it should be understood that fewer straps could be provided for each set. Preferably, there should be at least two straps for each of the sets; however, a single strap could be utilized provided it had sufficient width to provide stability to the pillow 40' it is to retain. Additionally, there could be a greater or lesser number of sets of straps depending on how many different positions it is desired for a patient's leg.

Figure 12:
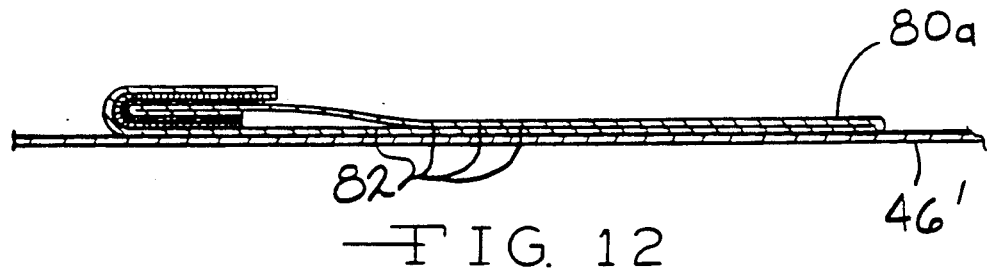
FIG. 12 is a sectional view taken through line 12—12 of FIG. 11.
Figure 13:
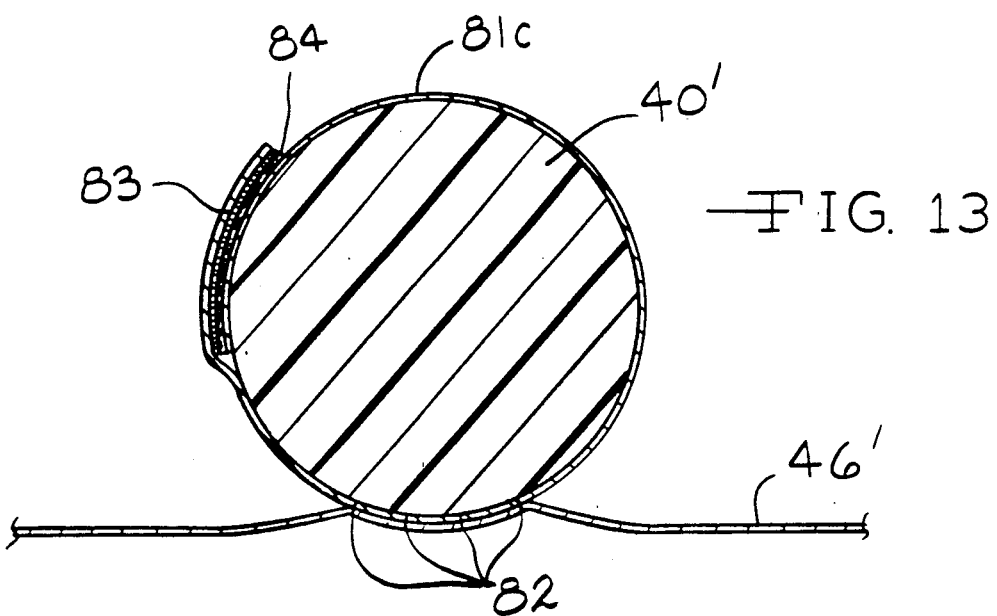
FIG. 13 is a sectional view taken through line 13—13 of FIG. 11.
Figure 14:
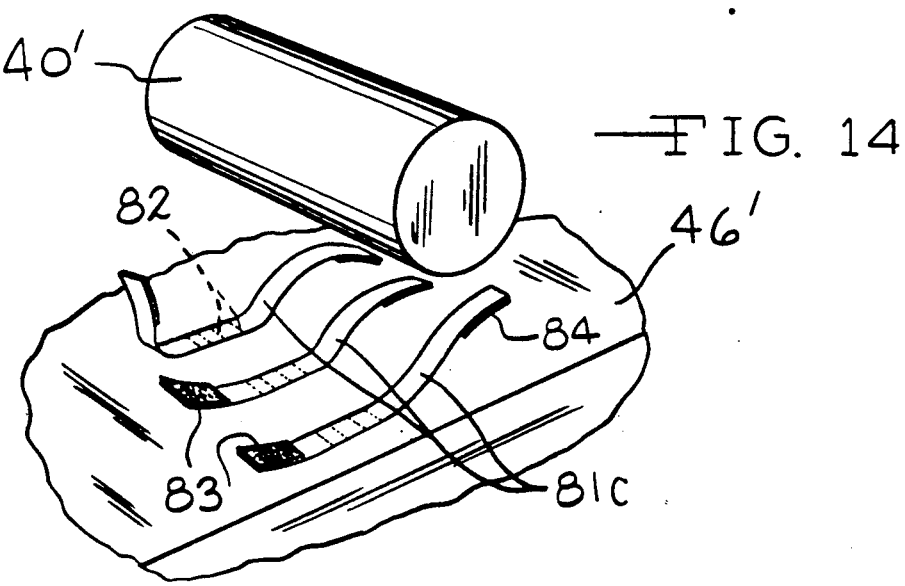
FIG. 14 is a fragmentary perspective of the modified embodiment of FIG. 11.

FIG. 12 is a sectional view taken through line 12—12 and showing one of the straps 80a fastened to the second sheet member 46' by means of sewn stitching 82 with its ends fastened together but without a pillow. FIG. 13 is a sectional view taken through line 13—13 showing an identical strap, in this case strap 81c, fastening the pillow 40' to the second sheet member 46'. FIG. 14 shows the position of the strap members 81c in an opened position preparatory to receiving the pillow 40'. The sewn stitching 82 can be clearly seen in FIGS. 13 and 14 along four separate lines of stitiching. Means other than sewn stitching may be utilized for fastening the straps 80a–81c to the panel 46'. For example, a suitable adhesive may be utilized or the straps 80a–81c may be fed through slots 90 in the panel 46' as shown in FIG. 15 with strap 81b. Each of the straps is provided with a first end 83 and a second end 84, each of which is formed of synthetic material which adheres when pressed together and is sold under the Trademark "VELCRO". Thus, the first end 83 may have loops and the second end 84 may have hooks. "VELCRO" fasteners are well-known in the art and perform no part of the present invention. It will be readily appreciated that other types of fastening means such as hooks or buckles could be utilized with the straps in place of the "VELCRO".

Preferably, the loops on the first end 83 are on one side of the straps while the hooks on the second end 84 are on the opposite side. Additionally, it is desired that the sewn stitching 82 not be located at the center of the straps 80a–81c but rather it be located closer to that end of the strap which is furthest removed from the aperture 53' or 54'. As may be seen in FIG. 13, this will result in the joined first and second ends 83 and 84 encircling and retaining a pillow 40' being located on the side opposite from the side which will be contacted by the patient's foot. Thus, the patient's foot may rest against the straps 80a–81c in an area away from the fastened first and second ends 83 and 84 thus, minimizing any discomfort to the patient.

Referring now to FIGS. 16 and 17, there is shown yet another embodiment which utilizes a different means for connecting the pillow or foot support to the cover sheet. The modified combination extremity sheet and leg holder 10a includes a first cover sheet 11a similar to the cover sheet 11 of the embodiment of FIGS. 1–7 and a pillow 91. The cover sheet 11a has at least one rectangular cutout 44a. As shown in FIG. 16, there are two rectangular cutouts 44a and 45a illustrating an embodiment which would be used for a patient having surgery on both knees at the same time. However, it should be understood that the embodiment of FIGS. 16 and 17 and the means for fastening a pillow 91 or other foot support to the sheet 11a may be used irrespective of whether it has one cutout 44a and is one intended for performing surgery on one leg of the patient or has two cutouts and is intended for performing surgery on both legs of a patient.

A panel member 46a is secured to the cover sheet 11a.

There is also provided a pair of cutouts 47a and 48a in the panel member 46a. Positioned within each of the cutouts 47a and 48a are a pair of identical thrid sheet members 49a and 50a. The sheet members 49a and 50a are formed of a thin sheet of rubber or other resiliently stretchable material and are each provided with an aperture 53a and 54a, respectively, each of which will receive a leg of a patient. The third sheet members 49a and 50a extend outwardly beyond their respective sets of aligned cutouts 44a, 47a and 45a, 48a and have their respective edge portions 51a, 52a adhesively connected or sewn or otherwise secured to the first cover sheet 11a or the panel member 46a or, preferably to both.

As can be seen in FIG. 16, a pillow 91 or other foot support means is aligned with one or both of the apertures 53a, 54a.

The modified means of supporting the pillow 91 on the cover sheet 11a may include cooperating hooks and loops, of the type previously described and sold under the trademark "VELCRO", one of which sets is adhesively or otherwise secured to the pillow 91 and the other of which is fastened to the cover sheet 11a, directly or indirectly. However, other types of fasteners may be used such as those marketed by the Industrial Specialties Division of 3M Corporation, St. Paul, MN and sold under its Registered Trademarks "Scotchmate" and "Dual Lock".

Thus, as can be seen in FIGS. 16 and 17, there are provided two loop members 92 formed as elongated strips indirectly fastened to the cover sheet 11a and extending in a direction parallel to the direction of a patient's leg and parallel to each other. The panel member 46a may have an elongated rectangular cutout 93 in which is positioned a plastic or other panel 94 which is impervious to liquids and which possesses sufficient strength to withstand, without tearing, the forces imparted to it by a patient's leg positioned on the pillow and the forces resulting from removal of the pillow 91 and its sets of hooks from the loop members 92. The plastic panel 94 may be adhered to the first sheet 11a but preferably has an outer edge 95 extending beyond the edge of the rectangular cutout 93 and is adhered to both the cover sheet 11a and the panel member 46a. If desired, panel member 46a and plastic panel 94 could be one and the same. Additionally, it is within the contemplation of the present invention that the loop members 92 could be attached directly to the cover sheet 11a rather than indirectly to it through the plastic panel 94.

The pillow 91 shown in FIGS. 16 and 17 has a rectangular cross-sectional configuration one surface of which has a pair of hook members 96 substantially at right angles to the longitudinal axis of the pillow 91 and spaced apart a distance which will permit each of the hook members 96 to engage one of the loop members 92 fastened to the plastic panel 94. Thus, as will be readily appreciated, under this embodiment, the pillow 91 may be continuously positionable over the loop members 92 in a number of positions away from the aperture 53a and a similar pillow (not shown) in a number of positions away from the aperture 54a. This embodiment also has the additional advantage of permitting the pillow to be rapidly and easily affixed and then moved and reaffixed.

It should be understood that there could be a greater or lesser number of loop members and hook members. Thus, it is possible to have a single loop member on the cover sheet 11a and a single hook member on the pillow 91 provided that they were of sufficient width to prevent undue deflection from engagement by the patient's foot or leg. Additionally, it is possible that the loop members 92 extend in a direction 90° from that shown in FIG. 16. In this event, the hook members 96 will be disposed parallel to the longitudinal axis of the pillow 91.

Referring now to FIG. 18, there is shown a pillow 97 having a generally circular cross-sectional configuration but having a flat side 98 on which are adhered the hook members 96. If desired, the pillow could have a triangular or any other desired cross-sectional configuration so long as there is one flat side to provide a surface for retaining the hook members of sufficient breadth and length to satisfactorily engage the loop members 92.

Figure 19:
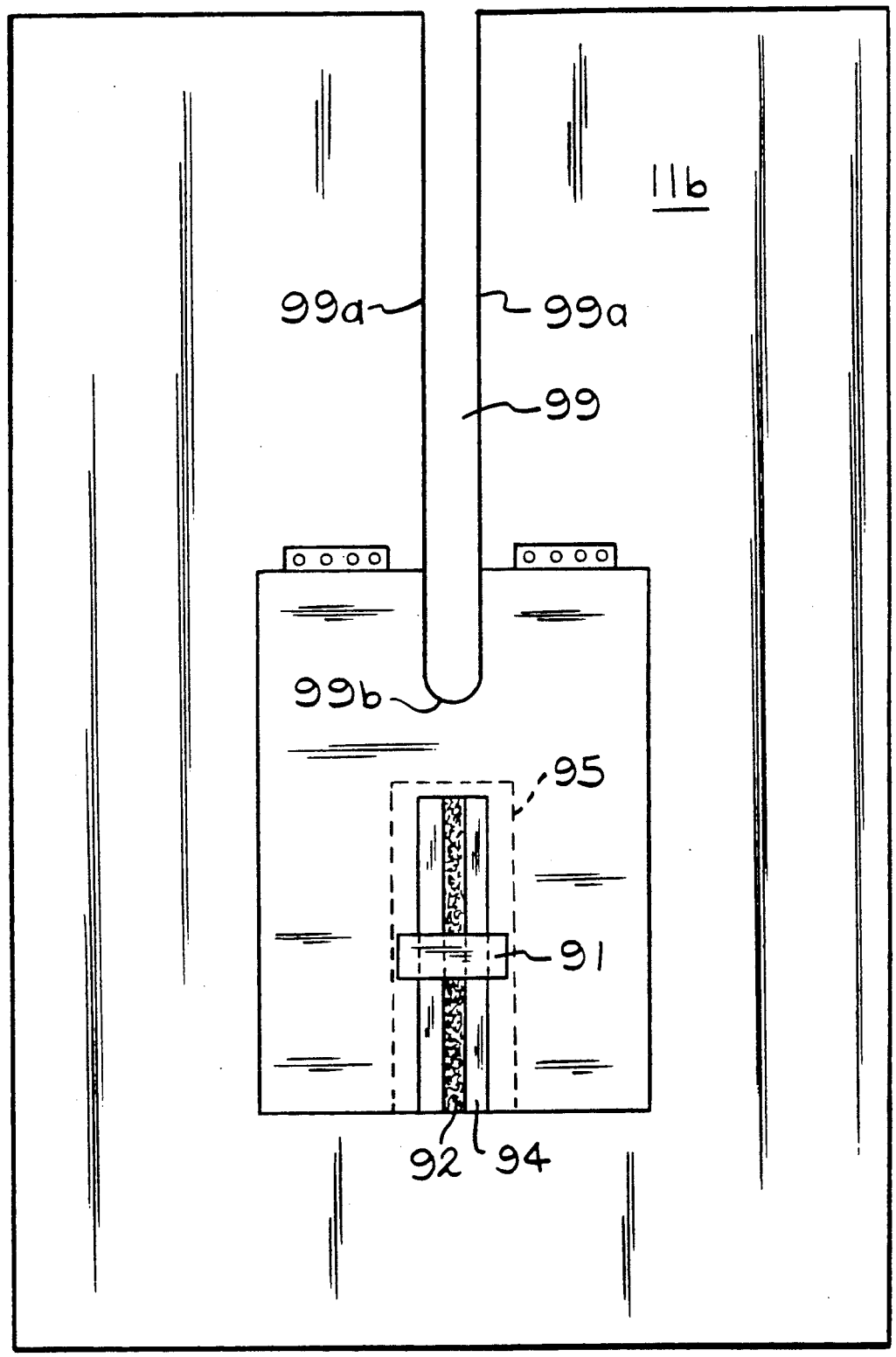
FIG. 19 is a top plan view of yet another embodiment.

Referring now to FIG. 19, there is shown yet another embodiment in which a cover sheet 11b is provided with an elongated cutout 99 for receiving the leg of a patient. The cutout 99 shown in FIG. 19 is defined by U-shaped edge having spaced apart parallel side edges 99a and a closed arcuate bottom 99b. However, it should be understood that the cutout 99 could have a wide variety of other shapes and could also simply be a slit through which the patient's leg may extend. Additionally, this type of cutout may be used in an extremity sheet suitable for operating on both legs of a patient at the same time in which case there will be provided two separate cutouts. Furthermore, it should be understood that this type of cutout may be used with any of the types of fastening means for the foot support disclosed in the various embodiments of the present application. Accordingly, as used in the appended claims, the term "cutout" is intended to include each of the embodiments disclosed herein for receiving a patient's leg through a cover, sheet or panel including but not limited to (a) a cutout in the form of a square, rectangle, circle or other geometric or annular configuration in which a peripheral edge encircles the cutout, (b) a cutout in the form of a slot having one end open and a periphery defined by straight or curved sides and a closed end and (c) a simple slit through which a patient's leg may extend.

Many variations in construction will be readily apparent to those skilled in the art. For example, a greater or lesser number of pockets or sets of straps may be provided. The description, construction, materials and dimensions are given only as examples and not by way of limitation. Depending upon the types of material used, the combination extremity sheet and leg holder can be disposible intended for a single use or reusable in which case it must be washable and sterilizable.

Many modifications will be readily apparent to those skilled in the art. Accordingly, the scope of the present invention should be limited only by the scope of the appended claims.

We claim:

1. A combination extremity sheet and leg support comprising:
   (a) a cover having a cutout of sufficient size to permit the leg of a patient to extend therethrough;
   (b) a panel fastened to said cover, said panel having a cutout of sufficient size to permit the leg of a patient to extend therethrough, said panel cutout being aligned with said cover cutout;
   (c) a plurality of pockets fastened to one of said cover and said panel, said pockets being spaced varying distances from said aligned cutouts and positioned to underlie the leg of a patient extending through said aligned cutouts; and,
   (d) foot support means sized to be positioned in each of said pockets.

2. A combination extremity sheet and leg support according to claim 1 further including a stretchable panel positioned in the aligned cutouts and affixed to at least one of said cover and said panel, said stretchable panel having an aperture of sufficient size to permit the leg of a patient to extend therethrough.

3. A combination extremity sheet and leg support according to claim 1 wherein said pockets are fastened to said panel.

4. A combination extremity sheet and leg support according to claim 1 wherein each of said cover and said panel have additional aligned cutouts positioned to receive the second leg of a patient and further including a plurality of additional pockets spaced varying distances from said additional aligned cutouts and positioned to underlie the leg of a patient extending through said additional aligned cutouts, and foot support means sized to be received in each of said additional pockets.

5. A combination extremity sheet and leg support according to claims 1, 2, 3 or 4 wherein said combination is disposable after a single use.

6. A combination extremity sheet and leg support according to claims 1, 2, 3 or 4 wherein said combination is re-usable, washable and sterilizable.

7. A combination extremity sheet and leg holder comprising:
   (a) a first sheet of flexible material sized to substantially cover a patient undergoing surgery, said first sheet having at least one cutout in a central portion thereof;
   (b) a second sheet of flexible material fastened to said first sheet, said second sheet having
     (i) a cutout aligned with said first sheet cutout, said aligned cutouts defining an aperture sized to permit the leg of a patient to extend therethrough and
     (ii) a plurality of pockets positioned to underlie by the straightened leg of a patient extending through said aperture; and
   (c) a pillow sized to be received in each of said pockets, the specific pocket receiving said pillow at any time being dependent upon the length of the patient's leg and the amount of bending desired for the knee.

8. A combination extremity sheet and leg support according to claim 7, further including a stretchable panel positioned in the aligned cutouts and affixed to at least one of said first sheet and said second sheet, said stretchable panel having an aperture of sufficient size to permit the leg of a patient to extend therethrough.

9. A combination extremity sheet and leg support according to claim 7, wherein each of said first sheet and said second sheet have additional aligned cutouts positioned to receive the second leg of a patient and further including a plurality of additional pockets spaced varying distances from said additional aligned cutouts and positioned to underlie the leg of a patient extending through said additional aligned cutouts, and foot support means sized to be received in each of said additional pockets.

10. A combination extremity sheet and leg support comprising:
    (a) a cover having a cutout of sufficient size to permit the leg of a patient to extend therethrough;
    (b) a panel fastened to said cover, said panel having a cutout of sufficient size to permit the leg of a patient to extend therethrough, said panel cutout being aligned with said cover cutout;
    (c) foot support means; and,
    (d) engagement means for fastening said foot support means to at least one of said cover and said panel in a position to underlie the leg of a patient extending through said cutouts.

11. A combination extremity sheet and leg support according to claim 10, wherein said engagement means includes at least one set of straps fastened to at least one of said cover and said panel and sized to engage said foot support means.

12. A combination extremity sheet and leg support according to claim 10, wherein said engagement means includes a plurality of sets of straps, said sets of straps being spaced varying distances from said cutouts.

13. A combination extremity sheet and leg support according to claim 10, wherein said engagement means includes cooperating sets of fastener members releasably engageable to each other, one of said sets fastened to said foot support means and the other of said sets fastened to said cover.

14. A combination extremity sheet and leg support according to claim 13, wherein the set of said fastener members fastened to at least one of said cover and said panel comprises at least one elongated strip substantially parallel to the leg of a patient extending through said aligned cutouts.

15. A combination extremity sheet and leg support according to claim 10 further including a stretchable panel positioned in the aligned cutouts and affixed to at least one of said cover and said panel, said stretchable panel having an aperture of sufficient size to permit the leg of a patient to extend therethrough.

16. A combination extremity sheet and leg support according to claim 10 wherein each of said cover and said panel have additional aligned cutouts positioned to receive the second leg of a patient and further including additional foot support means and additional engagement means for fastening said additional foot support means to at least one of said cover and said panel in a position to underlie the leg of a patient extending through said additional aligned cutouts.

17. A combination extremity sheet and leg support according to claim 16, wherein said additional engagement means includes at least one set of straps fastened to at least one of said cover and said panel and sized to engage said foot support means.

18. A combination extremity sheet and leg support according to claim 16, wherein said additional engagement means includes a plurality of sets of straps, said sets of straps being spaced varying distances from said additional aligned cutouts.

19. A combination extremity sheet and leg holder comprising:
   (a) a first sheet of flexible material sized to substantially cover a patient undergoing surgery, said first sheet having at least one cutout in a central portion thereof;
   (b) a second sheet of flexible material fastened to said first sheet, said second sheet having a cutout aligned with said first sheet cutout, said aligned cutouts defining an aperture sized to permit the leg of a patient to extend therethrough;
   (c) foot support means; and
   (d) a plurality of sets of engagement means for fastening said foot support means to at least one of said first and second sheets, the specific set of said engagement means fastening said foot support means at any time being dependent upon the length of the patient's leg and the amount of bending desired for the knee.

20. A combination extremity sheet and leg support according to claim 19, further including a stretchable panel positioned in the aligned cutouts and affixed to at least one of said first sheet and said second sheet, said stretchable panel having an aperture of sufficient size to permit the leg of a patient to extend therethrough.

21. A combination extremity sheet and leg support according to claim 19, wherein said engagement means includes sets of straps fastened to at least one of said first sheet and said second sheet and sized to engage said foot support means.

22. A combination extremity sheet and leg support according to claim 19, wherein each of said first sheet and said second sheet have additional aligned cutouts positioned to receive the second leg of a patient and further including a plurality of additional sets of engagement means spaced varying distances from said additional aligned cutouts and positioned to underlie the leg of a patient extending through said additional aligned cutouts.

23. A combination extremity sheet and leg holder comprising:
   (a) a sheet of flexible material sized to substantially cover a patient undergoing surgery, said sheet having at least one cutout to permit the leg of a patient to extend therethrough;
   (b) foot support means for maintaining at least a portion of the leg of a patient extending through said cutout in an elevated position; and
   (c) engagement means attached to said sheet and fastening fastening said foot support means to said sheet in a position to underlie the leg of a patient extending through said cutout.

24. A combination extremity sheet and leg support according to claim 23, wherein said engagement means includes at least one pocket sized to receive said foot support means.

25. A combination extremity sheet and leg support according to claim 24, wherein said foot support means comprises a pillow having gripping means at one end.

26. A combination extremity sheet and leg support according to claim 23, wherein said engagement means includes a plurality of pockets sized to receive said foot support means and spaced varying distances from said cutout, the specific pocket receiving said foot support means at any time being dependent upon the length of the patient's leg and the amount of bending desired for the knee.

27. A combination extremity sheet and leg support according to claim 23 wherein said engagement means includes at least one set of straps fastened to said sheet and sized to engage said foot support means.

28. A combination extremity sheet and leg support according to claim 23, wherein said engagement means includes a plurality of sets of straps, said sets of straps being spaced varying distances from said cutout, the specific set of straps engaging said foot support means at any time being dependent upon the length of the patient's leg and the amount of bending desired for the knee.

29. A combination extremity sheet and leg support according to claim 23, wherein said engagement means includes cooperating sets of fastener members, releasably engagable to each other, one of said sets fastened to said foot support means and the other of said sets fastened to said sheet of flexible material.

30. A combination extremity sheet and leg support according to claim 29, wherein the set of fastener members fastened to said sheet of flexible material comprises at least one elongated strip substantially parallel to the leg of a patient extending through said cutout.

31. A combination extremity sheet and leg support according to claim 29, wherein the set of fastener members fastened to said sheet of flexible material comprises at least two parallel elongated strips extending away from said cutout substantially parallel to the leg of a patient extending therethrough and the set of fastener members fastened to said foot support member comprises at least two parallel strips positioned to engage said set of fastener members fastened to said sheet of flexible material.

32. A combination extremity sheet and let support according to claim 29, wherein said foot support means has a planar surface to which one of said sets of fastener members is fastened.

33. A combination extremity sheet and leg support according to claim 23, further including a stretchable panel positioned in said cutout and affixed to said sheet, said stretchable panel having an aperture of sufficient size to permit the leg of a patient to extend therethrough.

34. A combination extremity sheet and leg support according to claim 23, wherein said sheet has an additional cutout positioned to receive the second leg of a patient and further including additional foot support means and additional engagement means for fastening said additional foot support means to said sheet in a position to underlie the leg of a patient extending through said additional cutout.

35. A combination extremity sheet and leg support according to claim 34, wherein said additional engagement means includes at least one pocket sized to receive said foot support means.

36. A combination extremity sheet and leg support according to claim 34, wherein said additional engagement means includes at least one set of straps fastened to said sheet and sized to engage said additional foot support means.

37. A combination extremity sheet and leg support according to claim 34, wherein said additional engagement means includes a plurality of additional sets of straps, said additional sets of straps being spaced varying distances from said cutouts, the specific one of said additional sets of straps engaging said additional foot support means at any time being dependent upon the length of the patient's leg and the amount of bending desired for the knee.

38. A combination extremity sheet and leg holder comprising:
(a) a sheet of flexible material sized to substantially cover a patient undergoing surgery, said sheet having at least one cutout to permit the leg of a patient to extend therethrough;
(b) foot support means for maintaining the leg of a patient extending through said cutout in any of a plurality of positions, each of which positions has at least a portion of said patient's leg elevated; and
(c) a plurality of sets of engagement means attached to said sheet and fastening fastening said foot support means to said sheet, the specific set of said engagement means fastening said foot support means at any time being dependent upon the length of the patient's leg and the amount of bending desired for the knee.

39. A combination extremity sheet and leg holder according to claim 38, wherein said engagement means includes a plurality of pockets sized to receive said foot support means.

40. A combination extremity sheet and leg holder according to claim 38, wherein said engagement means includes cooperating sets of fastener members, releasably engageable to each other, one of said sets fastened to said foot support means and the other of said sets fastened to said sheet of flexible material.

41. A combination extremity sheet and leg holder according to claim 40, wherein the set of fastener members fastened to said sheet of flexible material comprises at least one elongated strip substantially parallel to the leg of a patient extending through said cutout.

42. A combination extremity sheet and leg holder according to claim 40, wherein the set of fastener members fastened to said sheet of flexible material comprises at least two parallel elongated strips extending away from said cutout substantially parallel to the leg of a patient extending therethrough and the set of fastener members fastened to said foot support member comprises at least two parallel strips positioned to engage said set of fastener members fastened to said sheet of flexible material.

43. A combination extremity sheet and leg holder according to claim 38, wherein said foot support means has a planar surface to which one of said sets of fastener members s fastened.

44. A combination extremity sheet and leg support according to claim 38, wherein said engagement means includes sets of straps fastened to said sheet and sized to engage said foot support means.

45. A combination extremity sheet and leg support according to claim 38, further including a stretchable panel positioned in the said cutout and affixed to said sheet, said stretchable panel having an aperture of sufficient size to permit the leg of a patient to extend therethrough.

46. A combination extremity sheet and leg support according to claim 38, wherein said sheet has an additional cutout positioned to receive the second leg of a patient and further including a plurality of additional sets of engagement means spaced varying distances from said cutout and positioned to underlie the leg of a patient extending through said additional cutout.

* * * * *